United States Patent [19]
Quigley et al.

[11] Patent Number: 5,835,189
[45] Date of Patent: Nov. 10, 1998

[54] METHOD AND APPARATUS FOR ASSESSING AN OPHTHALMIC PATIENT BEFORE AND AFTER MEDICAL OR SURGICAL INTERVENTION SUCH AS LASER SURGERY

[76] Inventors: Michael G. Quigley, 388 Roslyn, Westmont, Quebec, Canada, H3Z 2L6; Howard B. Rosen, 1 Lyncroft Rd., Montreal PQ., Canada, H3X 3E3

[21] Appl. No.: 853,427

[22] Filed: May 9, 1997

[51] Int. Cl.$^6$ ............................................. A61B 3/00
[52] U.S. Cl. ............................................. 351/206
[58] Field of Search ................... 351/206, 212, 351/211; 600/558, 452; 482/117; 396/18

[56] References Cited

U.S. PATENT DOCUMENTS

| | | | |
|---|---|---|---|
| 5,137,029 | 8/1992 | Parra | 600/558 |
| 5,220,360 | 6/1993 | Verdooner et al. | 351/212 |

*Primary Examiner*—George Manuel
*Attorney, Agent, or Firm*—James H. Phillips

[57] ABSTRACT

In order to determine the prospective long term improvement to a diseased eye obtained by performing a treatment such as retinal laser surgery, the diameters of the four major arteriole blood vessels are measured, preferably digitally, and summed before the treatment at positions substantially equidistant from the center of the region where they converge and enter the optic nerve head. After the eye heals, the diameters of the blood vessels are digitally remeasured, and the degree of reduction of the second value with respect to the first value is determined. The reduction is compared to a predetermined reduction range (as obtained, for example, from a computer database of known results) which is representative of known degrees of long term improvement to obtain an indication of the expected long term results of the subject eye and the adequacy of the treatment. The same procedure may be employed to predict the results of medical or surgical retinal interventions other than retinal laser surgery, and a similar procedure may be employed to help establish the suitability of medical or surgical retinal interventions, including laser surgery, on a given eye by comparing the retinal blood vessel measurements taken before any such intervention to corresponding measurements of a reference eye (e.g., a normal eye) and applying a maximum acceptable difference between the two.

31 Claims, 4 Drawing Sheets

METHOD AND APPARATUS FOR ASSESSING AN OPHTHALMIC PATIENT BEFORE AND AFTER MEDICAL OR SURGICAL INTERVENTION SUCH AS LASER SURGERY

FIELD OF THE INVENTION

This invention relates to the medical arts and, more particularly, to a method for quickly establishing a benchmark value indicative of 1) the risk and rate of progression of retinal related diseases in a given ophthalmic patient and 2) the degree of efficacy obtained by a given medical or surgical intervention, including laser surgery.

BACKGROUND OF THE INVENTION

Laser surgery has become a relatively common technique used by highly skilled ophthalmic surgeons to perform a variety of procedures on diseased and traumatized eyes, particularly those with damage to the retina and its associated structure. A broad term of art encompassing the use of laser surgery in this manner is "photocoagulation". Depending upon the particular problem with a given eye, as determined by an extensive study which typically includes taking a series of photographs using a fundus camera, an ophthalmic surgeon will carry out a series of closely controlled burns in the eye structure region under treatment. The surgeon determines whether a series of burns in the region of localized damage is called for or, as is often the case, whether it is appropriate to effect a more extensive panretinal photocoagulation in which on the order of 1200 to 1600 laser burns are distributed substantially uniformly across the patient's entire retina (excepting for an area surrounding the optic nerve, the area responsible for central vision and areas where certain major blood vessels are situated) is made.

Close control of the treatment is obtained not only by the dexterity and judgment of the surgeon and the excellence of the equipment used, but also by the prior selection of the type of laser (e.g., argon), power level, duration of each burn (typically, a small fraction of a second up to 0.5 second per spot) and spot size (typically in the range 100 to 500 microns).

It may be noted that laser light is characterized by waves that are all in the same phase such that the beam of laser energy remains collimated along its path. The major source of heat in laser surgery is the retinal pigment epithelium which absorbs the light energy and converts it to heat. The resulting effect on retinal tissues is thermal coagulation; i.e., local heat destruction of retinal proteins. Thus, one advantage of laser surgery is that the heat generated by the laser remains precisely at the site of absorption.

Usually, the intent of laser surgery treatment of the retina is to induce regression of abnormal blood vessels or prevent their formation in the retina, optic nerve, iris or anterior chamber angle. One of the most often seen sources of such abnormality is diabetes, and laser treatment of diabetic patients has proven to be of enormous value in preserving the eyesight of diabetics or, at least, even in already seriously affected patients, in mitigating the rate at with eyesight deteriorates.

Notwithstanding the highly developed skills of qualified ophthalmic surgeons and the excellence and maturity of the equipment and technology used in carrying out laser ophthalmic surgery, there remain uncertainties in making an early determination, particularly quantitatively, as to how effective laser surgery performed on a given eye has been. Similarly, there remain uncertainties in the risk of a given eye to progress to more serious disease and in determining the timing for the laser surgery.

Similarly, the same problems and uncertainties arise in the context of contemplated and applied interventions, such as other retinal ablations and/or systemic medical therapies, to treat diseased retinas.

It is to the end of eliminating or greatly reducing such uncertainties that the present invention is directed.

Objects of the Invention

It is therefore a broad object of this invention to provide a method for making an improved and readily achieved assessment of an ophthalmic patient's eye(s) before laser surgery or medical therapy and for later determining the degree of improvement in the condition of the eye(s) achieved by such surgery.

It is a more specific object of this invention to provide such a method in which the diameter of certain blood vessels in the eye are measured. These measurements are compared against certain predetermined criteria to determine firstly the risk of the eye(s) of a given patient for disease progression and secondly the degree of efficacy of a given treatment.

In another aspect, it is an object of this invention to employ such method in conjunction with interventions other than laser surgery including other retinal ablations and/or systemic medical therapy.

In yet another aspect, it is an object of this invention to extend the method to build and use a computer database to systematize and facilitate use of historic information to base the assessments and determinations.

In still yet another aspect, it is an object of this invention to provide apparatus by which the method of the invention can be practiced.

SUMMARY OF THE INVENTION

Briefly, these and other objects of the invention are achieved by, before laser surgery is performed, indirectly measuring, at a selected position the diameter (or an equivalent dimension of least one blood vessel in the retina of the eye, a dimension which can be related to the diameter of the blood vessel) to obtain a first value. Preferably, the diameters of the four major blood vessels are measured substantially equidistant from the center of the region where they converge and enter/leave the optic nerve head, the four measurements being summed to obtain the first value. Thereafter, the laser surgery is performed, and the eye is allowed to heal for a suitable period, typically several weeks. Then, the diameters of the same vessel or vessels are remeasured at the same position(s) to obtain a second value, and the degree of reduction of the second value with respect to the first value is determined. The reduction observed is matched to a predetermined reduction range (as obtained, for example, from a database of known results) which is representative of a known degree of long term improvement.

The same procedure may be employed to predict the results of medical or surgical retinal interventions other than retinal laser surgery. A similar procedure may be employed to help establish the suitability of medical or surgical retinal interventions, including laser surgery, on a given eye by comparing the retinal blood vessel measurements taken before any such intervention to corresponding measurements of a reference eye and applying a maximum acceptable difference between the two.

Similarly, a variation of the procedure may be employed to determine the prognosis of a diseased eye to progress to a more deleterious state.

While it is preferred to use retinal arteries as the reference blood vessels, the retinal veins may also be employed, but consistency should be maintained in the comparison process; i.e., arteries are preferably compared to arteries and veins to veins.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

DESCRIPTION OF THE PREFERRED EMBODIMENT(S)

Figure 1:
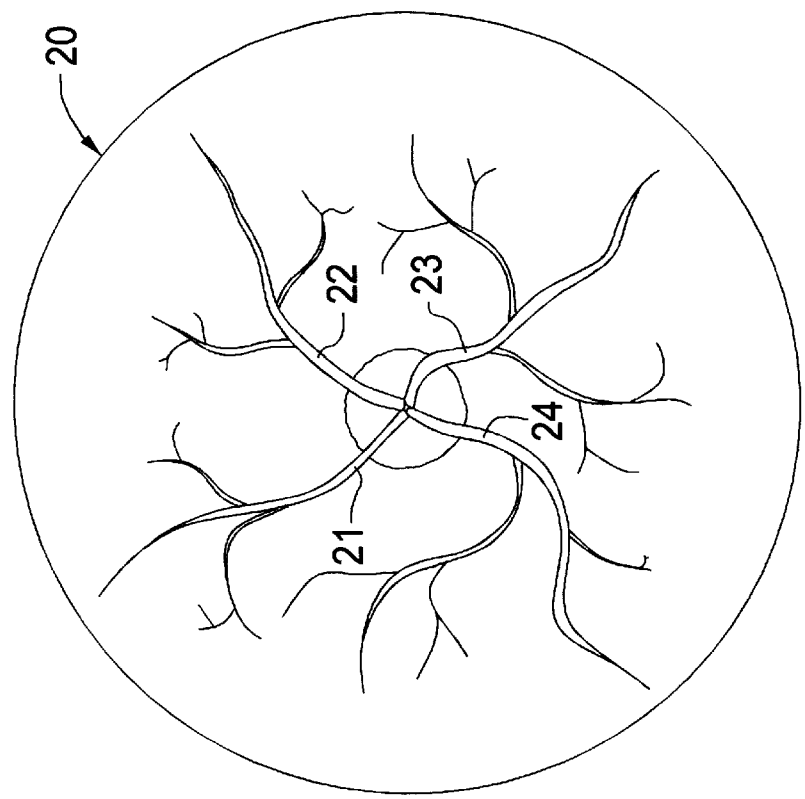
FIG. 1 is a view, as through a fundus camera, of a human eye retina particularly showing a relatively normal retinal vascularization.

For a full understanding of the invention, it is useful to have a fundamental understanding of the blood supply to the retina of an eye. Thus, referring to FIG. 1, which is a representation of a normal retina particularly showing the principal blood vessels, there is shown a fundus camera view of a retina 20 which is in an undamaged state. As is well known in the art, the retina receives and returns the majority of its blood supply from branches of central retinal vessels which, along with the optic nerve, extend from the back of the eye in an optic nerve sheath (not shown). It will be observed that the view of FIG. 1 is substantially centered about the region at which the optic nerve and the major vessels 21, 22, 23, 24 enter the optic nerve head. Of particular interest to a full understanding of the invention is that the vessels 21, 22, 23, 24 diverge outwardly, in a more or less quadrant pattern, across the retina 20. Each of the vessels 21, 22, 23, 24 have smaller branches which, themselves, have smaller branches serving to supply blood to and return blood from the retina to maintain its ongoing viability. In the following description, the configuration of the blood vessels 21, 22, 23, 24 and their main branches, as shown in FIG. 1 is used as a "benchmark", and the same general configuration is employed for the layout of the principal blood vessels in FIGS. 2, 3 and 4. As a practical matter, every eye has its own distinct vascular layout.

Consider now FIG. 2 which might be, for example only, the same eye illustrated in FIG. 1, but at a later period when considerable damage has taken place as a result of diabetes or any number of other conditions which cause such damage. Thus, it will be seen that the major vessels 21, 22, 23, 24 remain, as do their major branches, but a great deal of neo-vascularization has taken place as represented by numerous small vessels 25. In addition, several sites 26 of hemorrhaging are shown. As well known in the art, the sites of hemorrhaging and other vascular details are readily made clearly visible by employing conventional angiogram techniques.

An additional observation, directly relevant to the subject invention, is that the diameters of the major vessels 21, 22, 23, 24 are larger than in the corresponding vessels, at an earlier time (FIG. 1). The same is true of the branches from the major vessels, but, as will become apparent below, the use of this information is relatively easy to use when the major vessels themselves are considered.

It is necessary, in the presently preferred practice of the present invention, to accurately, but indirectly, measure the diameters of at least one, and preferably all four of, the major vessels 21, 22, 23, 24 at a reference position. Such a reference position can be obtained by, for example, indirectly (e.g., from a scaled photograph) measuring the diameters of the major vessels 21, 22, 23, 24 at an equal radius from the center of the region at which the major blood vessels enter or leave the retina. This radius, represented by the dashed circle 27, thus serves to establish the measuring positions for each of the four major blood vessels as indicated by the pairs 28 of facing arrows. Care must be taken, of course, to indirectly measure an actual diameter such that, in the example, the measurement of the blood vessel 23 is not made tangent to the imaginary circle 27, but is sufficiently skewed to ensure that it is the diameter of the blood vessel 23 which is measured at the reference position.

The measurements of the diameters of the major blood vessels 21, 22, 23, 24 may be performed manually (i.e., by direct observation of a fundus photograph by the surgeon) using a calibrated reticle or similar conventional device. Alternatively, a suitable scale may be established and a fundus photograph thereafter subjected to conventional digitization and image analysis to obtain the measurements.

It may be noted that, while it is not necessary to measure all four of the major blood vessels 21, 22, 23, 24, a summation of their diameters provides more reliable information, tending to average out slight deviations in the measuring process from vessel to vessel in a given eye. It may be further noted that one or more large branches of the major vessels could alternatively be measured, either separately or summed with measurements of the major vessels, but the most accuracy is usually obtained by measuring the major vessels themselves as described, and this is the presently preferred procedure.

Figure 2:
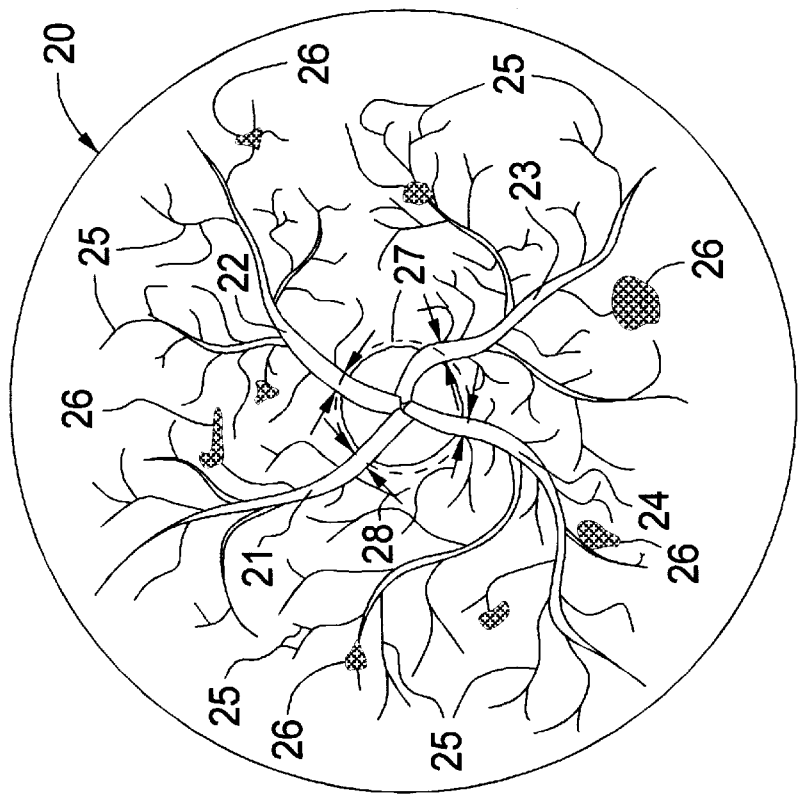
FIG. 2 is a view similar to FIG. 1 which shows an exemplary damaged human eye retina exhibiting hemorrhaging sites and neo-vascularization.
Figure 3:
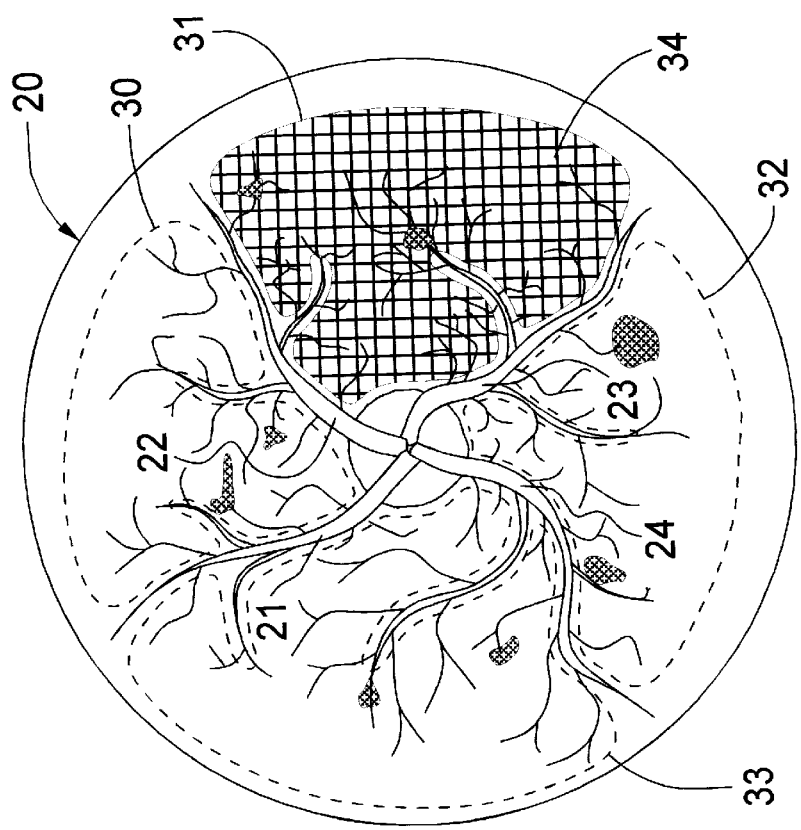
FIG. 3 is a view similar to FIG. 2 representing a laser treatment of the damaged eye retina.

Attention is now directed to FIG. 3 which generally illustrates a typical laser treatment for the damaged eye illustrated in FIG. 2. Areas 30, 31, 32 and 33 are laid out to define the areas between the four major vessels 21, 22, 23, 24 (and safely away from the optic nerve) and their major branches which will be subjected to a scatter burn. For example, the area at 31 may be laid out in a pattern (represented by the cross-hatch pattern 34) which spares the vessels 22 and 23 and their major branches in the area 31. As is well known in the art, scatter burns, in all the areas 30, 31, 32, 33, are carried out in one or more sessions as may be suitable for a given patient and individual eye.

Figure 4:
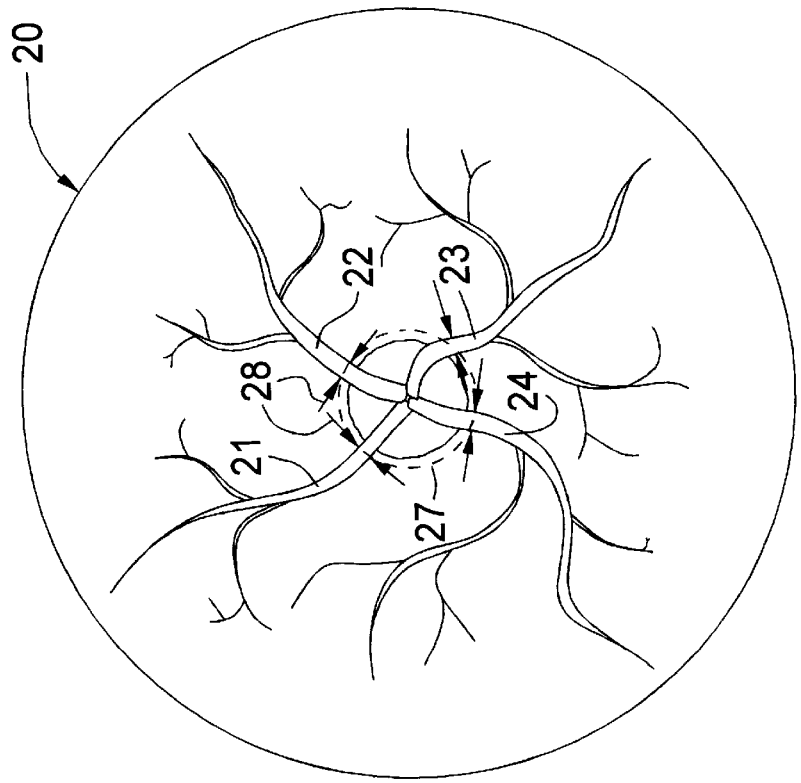
FIG. 4 is a view similar to FIG. 2 illustrating the effect of the laser treatment as observed after a suitable healing period and particularly showing an effect on the size of certain major blood vessels.

After a period of healing, as may be appropriate for a given eye, the fundus camera appearance of the treated retina 20 may assume that shown in FIG. 4. In accordance with the invention, another effect takes place which is directly relevant to the invention. The diameters of the major vessels 21, 22, 23, 24 will have been measurably reduced to a degree which can be related to the predicable long-term success of the treatment.

Figure 5:
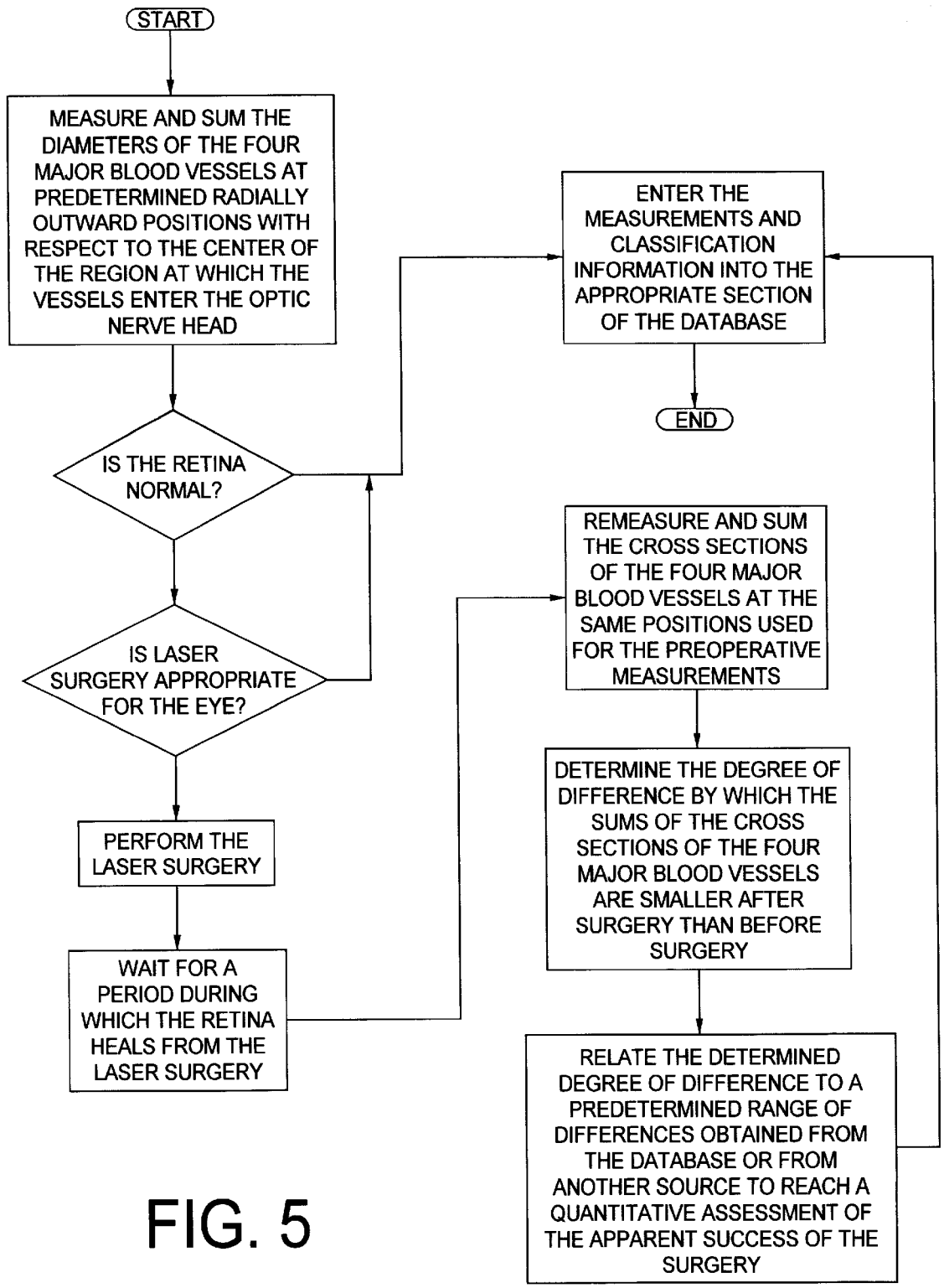
FIG. 5 is a flow chart of a presently preferred process for practicing the invention.

A high level flow chart of the presently preferred method embodiment of the invention is shown in FIG. 5. An eye is examined with a fundus camera or the like, and, typically, a series of photographs are made which are similar to FIGS. 1, 2, 3 and 4. Positions for one or more measurements on the major blood vessels (and/or their major branches) are determined as previously described. Preferably, the diameters of the four major vessels are indirectly (i.e., on the photographs) measured at a suitable radius from the center of the region at which the major vessels enter or exit the optic nerve head. The measurements are summed to reach a benchmark value for the eye under examination.

If the retina is determined to be normal, the diameters (individually or summed) are entered into a database in an appropriate category or section. The database may have as few or many categories as may be appropriate or desired. For example, measured eyes can be variously categorized by degree of damage, blood pressure, eye pressure and disease parameters (e.g., blood sugar, disease duration, etc.) and patient race, gender and age as such categories, alone or in combination, may prove valuable in determining the apparent success of the surgery and in predicting such success.

If the diseased eye is determined to not be a candidate for laser surgery, its measurements may nonetheless be suitably entered in the database if the information is useful in this context. Assuming that the diseased eye is determined to be a candidate for laser surgery, the surgery is performed in accordance with the surgeon's assessment and as previously described.

There follows a period of weeks during which the burns effected by the laser surgery is allowed to heal. On a subsequent examination, the diameters of the previously measured blood vessel(s) is/are measured again, and the results are compared against before and after criteria already in the database for other, comparable eyes. It may be noted that a decreased diameter observed in the blood vessels will produce the desired effect of attenuating blood pressure within the vessels. Finally, the post operative diameter(s) are entered into the database.

It will therefore be clear to those skilled in the art that, as more entries are made in the database, including actual determinations of the success of individual surgeries obtained by long term tracking, the database becomes more accurate and reliable.

Figure 6:
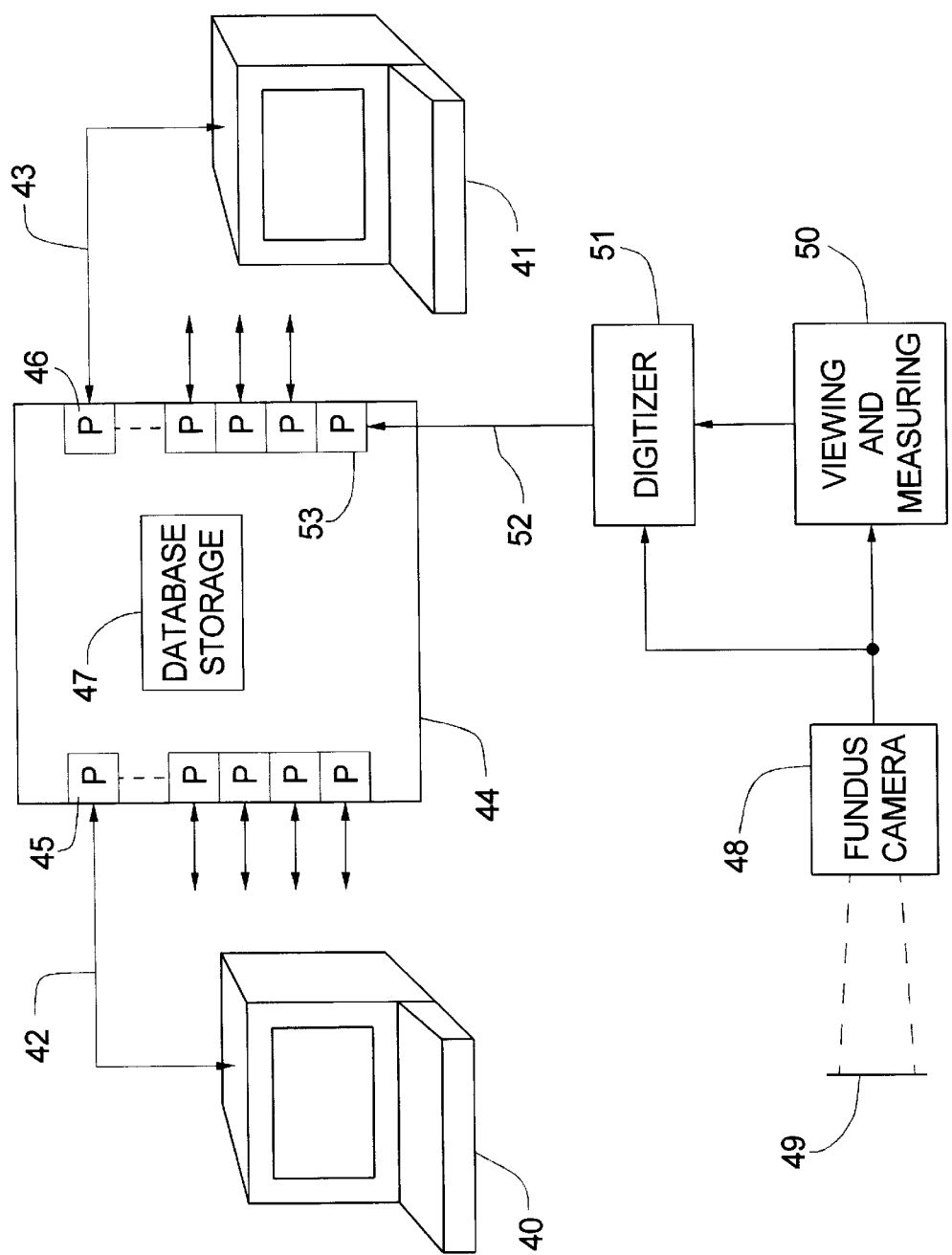
FIG. 6 is a representation of a data processing system used in the determination and measuring processes illustrated in FIGS. 2 and 4 and according to the preferred process as carried out according to the flow chart of FIG. 5.

FIG. 6 is a system block diagram of an exemplary data processing system for establishing, building and using a database by which the practice of the invention may be facilitated and refined. In the example shown, a network configuration is contemplated although a local system is equally applicable to the practice of the invention. One or more terminals, personal computers, work stations, etc., such as the personal computers 40, 41, communicate with a mass storage device 44 which includes a database 47. For example, the personal computers 40, 42, may bilaterally communicate with the mass storage device 44, respectively, via path 42 and port 45 and via path 43 and port 46. Other devices, not shown, may be incorporated into the system through the remaining ports or by other conventional means.

A fundus camera 48 permits observation of the retina 49 of a patient as previously described to obtain a view as exemplified by FIGS. 1–4. This view may be studied and the selected blood vessels measured by measuring and viewing apparatus 50 which is coupled to receive the view from the fundus camera 48 and may be incorporated therewith or be a separate device. As well known in the art, photographs may be obtained from the fundus camera 48 and/or the measuring and viewing device 50. The view from the fundus camera may also be directly applied to a digitizer 51 and/or may be indirectly applied to the digitizer via viewing and measuring apparatus 50. The digitizer 51 conventionally digitizes the current view applied as an input and places it in a suitable format for digital analysis and for storage in the database 47 via communications path 52 and port 53. Additional information relevant to the view, e.g., the appropriate category of the database in which the view and the supporting information (such as patient name, gender, age, eye identification, type of disease if any, physician, etc.) which should be stored may be entered by using one of the personal computers 40, 41 or by the use of data entry apparatus 54 coupled to the digitizer 51 or by any other suitable means.

In use, measurements of the diameters of the four major retinal blood vessels of a given eye (or as many of the major vessels as possible) are entered into an appropriate category in the database with supporting information. If laser surgery is performed, the four major retinal blood vessels are remeasured after recovery, and this information is compared with corresponding information in the database and is also itself entered in the database. The patient is monitored for a suitable period to obtain actual confirmation of the long term success of the laser surgery, and this information is also entered into the database. By this ongoing procedure, the content of the database is refined as more information is entered, and the prognosis for a good long term result from laser surgery on a given eye can be made with substantial confidence by relating the diameters of the major blood vessels before laser surgery to the diameters after surgery and a suitable healing period with reference to an appropriate category in the database to which the patient belongs.

A feature of the exemplary system shown in FIG. 6 is that, because a fundus image of a retina is digitized, computerized digital measuring techniques, such as those used in the interpretation of satellite images and the like, may be employed to automatically and very accurately obtain the desired measurements, thus eliminating some of the inherent uncertainties and inconsistencies of manual measurements taken be different observers and also substantially increasing the speed of the process.

The invention has been described in the context of laser surgery which is the readiest application at the state of the art. However, the degree of long term improvement obtained by other medical or surgical interventions on diseased eyes may be similarly predicted based on the diminution of the diameters of retinal blood vessels in accordance with historical information entered into a suitable database.

Similarly, the prognosis for a given diseased eye to progress to a more deleterious state may be determined by measuring the blood vessels of the eye and comparing it to examples in the database in the same category as the patient. This procedure can be carried out independent of any contemplated treatment.

It will be understood that the exemplary data processing system shown in FIG. 6 is one of many which can be employed to practice the invention. For example, a more simple, local system can include a single personal computer in which the mass memory unit 44 is integral (e.g., a hard drive), the digitizer being coupled to an input to the personal computer.

As previously mentioned, while it is presently preferable to use retinal arteries as the reference blood vessels, the retinal veins may also be employed, but consistency should be maintained in the comparison process; i.e., arteries are preferably compared to arteries and veins to veins.

Thus, while the principles of the invention have now been made clear in an illustrative embodiment, there will be immediately obvious to those skilled in the art many modifications of the structure, arrangements, proportions, elements, materials, and components, used in the practice of the invention which are particularly adapted for specific environments and operating requirements without departing from those principles.

What is claimed is:

1. A method for assessing the adequacy of a treatment for a diseased eye of a patient, the method comprising the steps of:
   A) before the treatment is carried out:
      1) obtaining a first view of the eye's retina;
      2) digitizing the first view; and
      3) in the first view, digitally measuring, at a selected position on at least one blood vessel in the retina, a dimension which can be related to the diameter of the blood vessel, obtaining a first value therefor;
   B) carrying out the treatment;
   C) after the treatment is carried out:
      1) obtaining a second view of the eye's retina;
      2) digitizing the second view; and
      3) in the second view, digitally measuring, at the selected position, the dimension of the blood vessel, obtaining a second value therefor;
   D) determining the reduction of the second value compared to the first value; and
   E) matching the reduction determined in step D) to a predetermined reduction range resident in a database to access the adequacy of the treatment.

2. The method of claim 1 in which the dimension is the diameter of the blood vessel.

3. The method of claim 2 in which the four major blood vessels are digitally measured, during each of steps A)3) and C)3), substantially equidistant from the center of the region where they converge and enter the optic nerve head and in which the measurements are summed to obtain the first and second values.

4. The method of claim 3 in which the predetermined reduction range is obtained from a computer database including historical information pertaining to measurements taken from other patients and to the actual long term results achieved by carrying out the treatment on the eyes of such other patients.

5. The method of claim 4 in which the first and second values are entered into the computer database with supporting information categorizing the patient.

6. The method of claim 5 in which the treatment is laser surgery.

7. The method of claim 4 in which the treatment is laser surgery.

8. A method for determining the suitability of employing a treatment on a diseased eye of a patient, the method comprising the steps of:
   A) obtaining a view of the eye's retina;
   B) digitizing the view;
   C) in the view, digitally measuring, at a selected position on at least one blood vessel in the retina, a dimension which can be related to the diameter of the blood vessel, obtaining a patient value therefor;
   D) determining a category representative of the patient;
   E) obtaining from a database, a reference value for a reference eye measured in the selected position;
   F) determining the difference by which the patient value exceeds the reference value;
   G) comparing the difference determined in step F) to a predetermined maximum difference; and
   H) if the difference determined in step F) exceeds the predetermined maximum difference, concluding that the patient is not a suitable candidate for the treatment.

9. The method of claim 8 in which, during step C), the diameters of the four major blood vessels are digitally measured substantially equidistant from the region where they converge and enter the optic nerve head and in which the measurements are summed to obtain the patient value.

10. The method of claim 9 in which the predetermined reduction range is obtained from a computer database including historical information pertaining to measurements taken from other patients and to the actual long term results achieved by carrying out the treatment on the eyes of such other patients.

11. A method for assessing the adequacy of a treatment for a diseased eye, the method comprising the steps of:
   A) before the treatment is carried out, measuring, at a selected position on at least one blood vessel in the retina of the eye, a dimension which can be related to the diameter of the blood vessel, obtaining a first value therefor;
   B) carrying out the treatment;
   C) waiting for the eye to heal from the effects of the treatment;
   D) remeasuring, at the selected position, the dimension of the blood vessel, obtaining a second value therefor;
   E) determining the reduction of the second value compared to the first value; and
   F) comparing the reduction determined in step E) to a predetermined reduction range to assess the adequacy of the treatment.

12. The method of claim 11 in which the dimension is the diameter of the blood vessel.

13. The method of claim 12 in which the diameters of the four major blood vessels are measured substantially equidistant from the center of the region where they converge and enter the optic nerve head and in which the measurements are summed to obtain the values.

14. The method of claim 13 in which the reduction range is obtained from a database including historical information pertaining to measurements taken from other patients and to the actual long term results achieved by carrying out the treatment on the eyes of such other patients.

15. The method of claim 14 in which the treatment is laser surgery.

16. The method of claim 14 in which information representative of the values is entered into the database.

17. The method of claim 13 in which the treatment is laser surgery.

18. The method of claim 17 in which information representative of the actual long term improvement of the eye is entered into the database.

19. The method of claim 12 in which the treatment is laser surgery.

20. The method of claim 11 in which the four major blood vessels are measured substantially equidistant from the center of the region where they converge and enter the optic nerve head and in which the measurements are summed to obtain the values.

21. The method of claim 20 in which the reduction range is obtained from a database including historical information pertaining to measurements taken from other patients and to the actual long term results achieved by carrying out the treatment on the eyes of such other patients.

22. The method of claim 21 in which the treatment is laser surgery.

23. The method of claim 22 in which information representative of the actual long term improvement of the eye is entered into the database.

24. The method of claim 21 in which information representative of the values is entered into the database.

25. The method of claim 20 in which the treatment is laser surgery.

26. The method of claim 11 in which the reduction range is obtained from a database including historical information pertaining to measurements taken from other patients and to the actual long term results achieved by carrying out the treatment on the eyes of such other patients.

27. The method of claim 26 in which the treatment is laser surgery.

28. The method of claim 27 in which information representative of the actual long term improvement of the eye is entered into the database.

29. The method of claim 26 in which information representative of the values is entered into the database.

30. The method of claim 11 in which the treatment is laser surgery.

31. Apparatus for assessing an individual eye of an individual patient comprising:
A) a computer;
B) a memory coupled to said computer;
C) a database stored in said memory, said database storing information including:
 1) categories of patients;
 2) the medical condition of individual eyes of other patients; and
 3) measurements of at least one blood vessel in the retina of each individual eye of the other patients;
D) camera means for obtaining an image of a the retina of the individual eye of the individual patient;
E) viewing and measuring means for observing the image and for manually obtaining the measurements for the individual eye of the individual patient;
F) digitizing means for receiving said image and for digitizing said image for digital analysis and for storage of the results of the digital analysis in said database; and
G) means for entering the results of the digital analysis and information pertaining to the category of the individual patient in said database.

* * * * *